(12) United States Patent
Page

(10) Patent No.: US 11,931,172 B2
(45) Date of Patent: Mar. 19, 2024

(54) CIRCADIAN SENSOR SYSTEM

(71) Applicant: Blue Iris Labs, Fairfax, CA (US)

(72) Inventor: Erik Russell Page, Fairfax, CA (US)

(73) Assignee: Blue Iris Labs, Inc., Fairfax, CA (US)

( * ) Notice: Subject to any disclaimer, the term of this patent is extended or adjusted under 35 U.S.C. 154(b) by 284 days.

(21) Appl. No.: 17/146,609

(22) Filed: Jan. 12, 2021

(65) Prior Publication Data

US 2022/0061758 A1    Mar. 3, 2022

Related U.S. Application Data

(60) Provisional application No. 62/963,490, filed on Jan. 20, 2020.

(51) Int. Cl.
*A61B 5/00* (2006.01)
*A61B 5/16* (2006.01)
(Continued)

(52) U.S. Cl.
CPC .......... *A61B 5/6801* (2013.01); *A61B 5/0004* (2013.01); *A61B 5/163* (2017.08);
(Continued)

(58) Field of Classification Search
CPC ..... A61B 5/6801; A61B 5/0004; A61B 5/163; A61B 5/4088; A61B 5/7264;
(Continued)

(56) References Cited

U.S. PATENT DOCUMENTS

2005/0272046 A1* 12/2005 Schermer ............. G01N 21/253
435/808
2010/0174345 A1*  7/2010 Ashdown ............... H05B 45/22
607/88
(Continued)

FOREIGN PATENT DOCUMENTS

CN          104429162 B   * 10/2017   ............ A61M 21/02
KR       20100027186 A   *  3/2010   ........... A61N 5/0618

OTHER PUBLICATIONS

Machine English Translation of KR 20100027186 A, Ashdown, Published 2010, pp. 1-16 (Year: 2010).*

(Continued)

*Primary Examiner* — Devin B Henson
*Assistant Examiner* — Matthew Eric Ogles
(74) *Attorney, Agent, or Firm* — Clifton Leon Anderson

(57) ABSTRACT

A circadian health system (CHS) provides for improving the health of Alzheimer's patients and other persons by controlling their exposure to circadian lighting. Circadian sensor devices (CSDs) are distributed in a living space, e.g., at about eye-level positions on respective walls of room. Each CSD includes a spectral sensor for measuring the intensity of light at various wavelength bands. Captured spectra can be compared to circadian light signatures so that the sources of circadian light can be identified. The identifications then allow predetermined high-resolution, e.g., 5 nm, spectra in the circadian wavelengths of 450-500 nm to be determined. The spectra can then be used to control circadian lighting to provide prescribed doses of circadian stimulus.

26 Claims, 3 Drawing Sheets

(51) Int. Cl.
*A61M 21/00* (2006.01)
*A61M 21/02* (2006.01)
*A61N 5/06* (2006.01)

(52) U.S. Cl.
CPC .......... *A61B 5/4088* (2013.01); *A61B 5/7264* (2013.01); *A61M 21/02* (2013.01); *A61N 5/0618* (2013.01); *A61B 2560/0214* (2013.01); *A61M 2021/0044* (2013.01); *A61M 2205/3306* (2013.01)

(58) Field of Classification Search
CPC .... A61B 2560/0214; A61B 2560/0242; A61B 5/0077; A61B 5/4809; A61B 5/1113; A61M 21/02; A61M 2021/0044; A61M 2205/3306; A61M 2021/005; A61M 2205/3313; A61M 2205/3327; A61M 2205/3561; A61M 2205/3576; A61M 2205/587; A61N 5/0618
See application file for complete search history.

(56) References Cited

U.S. PATENT DOCUMENTS

| | | | |
|---|---|---|---|
| 2013/0301034 A1* | 11/2013 | Olds | H05B 47/11 356/218 |
| 2015/0022093 A1* | 1/2015 | Smith | A61N 5/0618 315/307 |
| 2019/0223270 A1* | 7/2019 | Wingren | H05B 47/11 |
| 2020/0132547 A1* | 4/2020 | Yu | G01J 3/0264 |
| 2021/0010857 A1* | 1/2021 | Wingren | G01J 1/60 |

OTHER PUBLICATIONS

Machine English Translation of CN 104429162 B, Barosso, Published 2017, pp. 1-11 (Year: 2017).

* cited by examiner

CIRCADIAN SENSOR SYSTEM

BACKGROUND

Older Americans (65+) numbered 44.7 million in 2013, representing 14.1% of the U.S. population, and by 2030 this older population is estimated to grow to about 72 million. Furthermore, this population is living longer; people reaching age 65 have an average life expectancy of an additional 19.3 years. Of the 65+ population, 3.4% lived in nursing homes in 2013. If current trends continue, by 2030 this number will rise to about 10%.

Dementia is a progressive, degenerative disease of the brain. There is no known cure, and there are very few effective treatments. Alzheimer's disease (AD), the most common form of dementia, is the sixth-leading cause of death in the U.S. and the fifth-leading cause of death for those over the age of 65. It is projected that 13.8 million Americans will have AD or a related dementia disorder (ADRD) by 2050.

More than 70% of people with this disease live at home, and family members and friends provide almost 75% of the required care. As the disease progresses, families are often forced to move loved ones from home to assisted living facilities. Often, the precipitating factor is disturbed sleep-wake (circadian) cycles, where the person with AD/ADRD is awake at night, causing stress and fatigue to caregivers.

DETAILED DESCRIPTION

Figure 1:
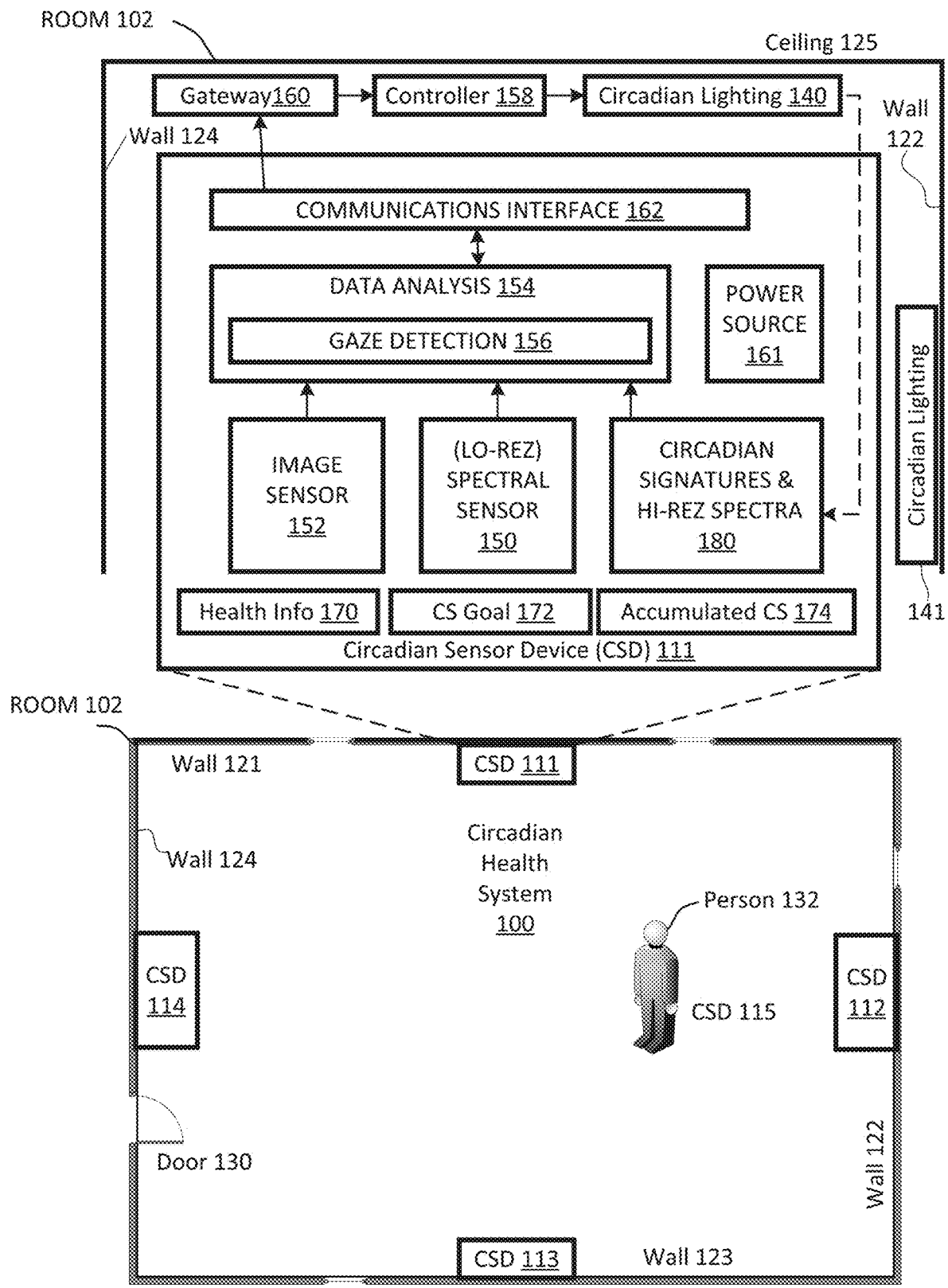
FIG. 1 is a schematic diagram of a circadian health room equipped with a circadian sensor system.

The present invention provides a circadian health system (CHS) that uses multiple circadian sensor devices (CSDs) to track a person's exposure to circadian light; the tracked information can be used to control that person's daily exposure to circadian light. As shown in the lower portion of FIG. 1, a circadian health system (CHS) 100 is shown deployed in a room 102. CHS 100 includes circadian sensor devices (CSDs) 111-114, mounted on respective walls 121-124 of room 102, which also includes a door 130 for ingress and egress. At the time represented in FIG. 1, there is a person 132 in the room wearing a wearable CSD 115. As shown in the upper portion of FIG. 1, a circadian lighting system 140 is mounted on the ceiling 125 of room 102.

Each of CSDs 111-115 includes a spectral sensor 150, as shown for CSD 111, for determining light spectra in their respective vicinities; in particular, the spectrum at the position of person 132 in room 102 can be determined by the spectral sensor 150 in CSD 115, assuming that person 132 is actually wearing CSD 115. However, since person 132 may not necessarily be wearing CSD 115, each of CSDs 111-114 includes an image sensor 152 so that the position and gaze orientation of person 132 in room 102 can be determined. Other embodiments use Bluetooth Low Energy (BLE) beacons and other wireless location systems to determine a person's location in a room. The intensity and spectral information from spectral sensors 111-114 can then be used, e.g., using triangulation and/or calibration data, to estimate the spectral characteristics at the person's position.

The effectiveness of circadian lighting on health is most closely related to the light the person actually sees. Thus, a person can benefit more from looking out a window during daytime than from facing a dark corner. Accordingly, data analysis functions 154 of CSDs 111-114 include a gaze detection function 156, e.g., similar to eye detection functions in eye autofocus systems used in some cameras. Alternatively, the data analysis can be performed by circadian lighting controller 158, with which CSDs can communicate via gateway 160. The person's position and gaze direction can be tracked along with the spectral readings from CSDs 111-114 to determine an effective total amount of circadian light seen by person 132; the effective total amount of light can be used to determine how to control circadian lighting system 140 to ensure that person 132 receives a sufficient dose of circadian light, e.g., daily. Power for the CSDs can be provided by a power source 161, e.g., a battery.

Wearable CSD 115 can be used to track circadian light received by person 132 when outside room 102. After all, if person 132 takes a walk outside on a sunny day, the need for additional circadian light when in room 102 may be reduced. When person 132 enters room 102, wearable CSD 115 can communicate its data to controller 158 for circadian lighting 140 via gateway 160, e.g., using a respective communications interface 162. Wearable CSD 115 can be programmed to identify its user, so that personalized health data, including health information 170, a circadian stimulus daily goal 172, and accumulated circadian stimulus 174 (for the current 24-hour period) can be used to control circadian lighting 140. The health information can be stored on the wearable CSD 115, controller 158, and/or stored in the cloud. Examples of wearable CSDs can include watches and smart glasses.

Fixed CSDs 111-114 can communicate to controller 158 via gateway 160 using their respective communications interfaces 162. The communicated data received by controller 158 can then be combined across CSDs 111-115. The combined information can then be used to control circadian lighting 140 to optimize the health of person 132, e.g., by sending commands and/or data from controller 158 to circadian lighting 140.

Different people can have different melatonin responses from light exposure, and these differences can be significant, e.g., the sensitivity can vary by two times and up to ten times. The invention provides for tailoring CS exposures based on melatonin levels. When more than one CS target is in the room, an algorithmic approach can be used, taking into account such factors as "doing the most good for the most people" and "focusing on the needs of the neediest people".

To optimize circadian treatments, the circadian spectrum seen by the person should be known precisely. The visible spectrum ranges from about 400 nanometers (nm) to about 780 nm. The range for circadian light is from about 450-500 nm (in the blue range), for which a resolution of 5 nm is desired for calculating circadian stimulus (CS) and other parameter values of interest such as melatonin suppression and phase shift. Accordingly, spectral sensors with 10 or more spectral bands over the 450-500 nm range can be used.

In the illustrated embodiment, spectral sensors 111-115 are commercially available 11-band visible light sensors, which provide effectively only three to four bands in the 450-500 nm range for circadian wavelengths. To obtain high (5 nm) spectral data using the relatively low resolution (15 nm) resolution of the spectral sensors, each CSD is programmed with spectral data 180 including: 1) the high-resolution (hi-rez) spectral characteristics of circadian lighting 140 and 2) a low-resolution (low-rez) spectral signature for circadian lighting 140. Such data can be generated using a calibration and/or setup procedure. Alternatively, at least the high-resolution spectral characteristics for the circadian lighting may be available from a vendor of the circadian lighting. The circadian signature can be applied to assess the contribution of the circadian lighting to an as-measured spectrum, while the high-resolution spectral data can be applied to the contribution to provide the desired high-resolution spectrum to which person 132 is being exposed.

Figure 2:
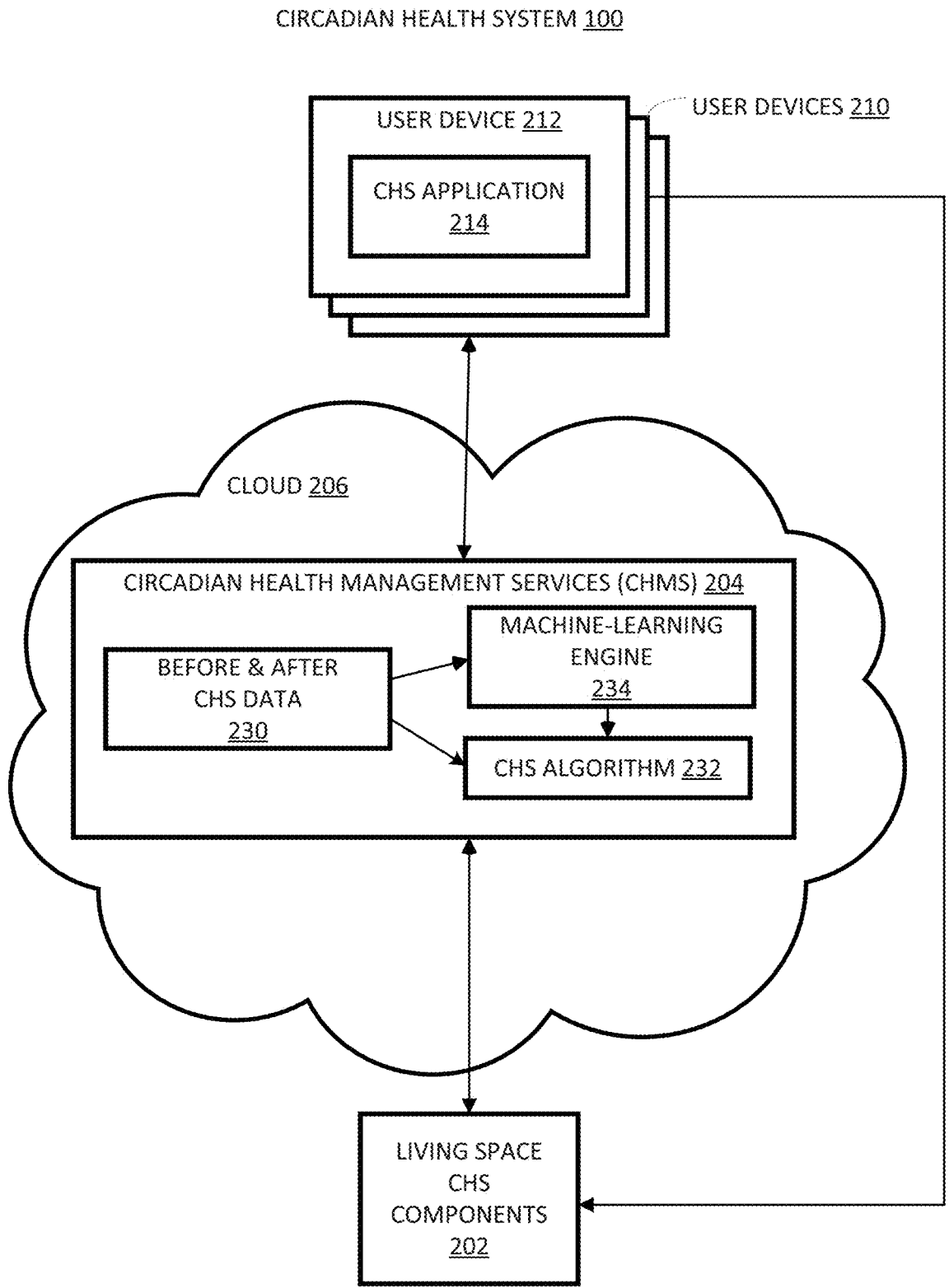
FIG. 2 is a flow chart of a circadian sensor process implementable in the circadian sensor system of FIG. 1 and other systems.

From the higher-level perspective of FIG. 2, it can be seen that CHS 100 includes living-space CHS components 202, circadian health management services 204 in the cloud 206. Living-space CHS components 202 are basically those components shown in FIG. 1, including devices in or near room 102. Circadian health management services 204 is coupled to living space CHS components 202 via Internet of Things (IoT) gateway 160 (FIG. 1), to receive spectral data and circadian lighting control data from these components and to control circadian lighting 140, 141. Patient/subject health data can be input to services 204 (FIG. 2) using a user device 212 running a CHS application 214, versions of which can be web-based or run on a smartphone or tablet OS.

CHMS 204 receives, e.g., from user devices 212, patient health data 230 both before and after patient exposures to circadian lighting. Data 230 is input to a CHS algorithm 232, which determined a dosage schedule for a patient. The dosage schedule is used to determine commands sent to control circadian lighting, e.g., 140 and 141 of FIG. 1. In addition, heath data 230 received after an exposure can be used to evaluate the effectiveness of a circadian dosage schedule. CHMS 204 includes a machine-learning engine 234 to optimize CHS algorithm 232 based on dosage effectiveness.

Figure 3:
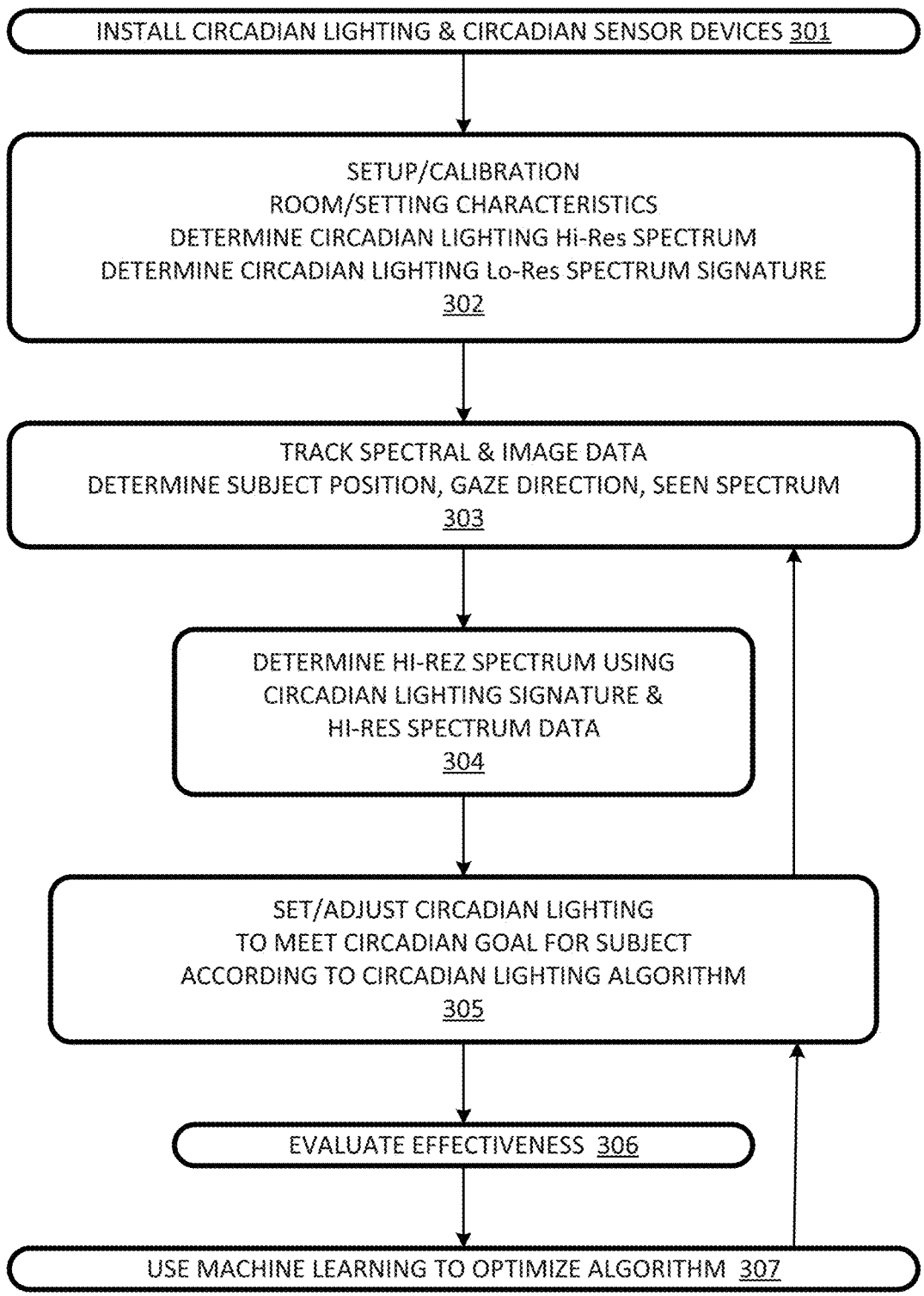
FIG. 3 is a schematic diagram of closed loop lighting control using the circadian sensor systems of FIG. 1.

A circadian sensor process 300 is flow-charted in FIG. 3. At 301, circadian lighting and circadian sensor devices are installed in a room or other space. Typically, the circadian lighting is installed on a ceiling, while sensors are installed in positions to measure light from the circadian lighting. Some embodiments use floor-standing, table-top, wall-mounted and other support structures for, e.g., eye-level, circadian lighting. Sensors may number two or more, with one on each of four walls being typical. More sensors can be used for rooms with complex shapes or line-of-sight obstacles such as partitions. In some cases, sensors can be mounted on ceilings or other support systems. While in the illustrated embodiments, spectral and image sensors share the same housing, in other embodiments, image sensors and spectral sensors can have separate housings and be placed at different locations; in some such embodiments, the number of image sensors need not equal the number of spectral sensors.

In addition, a wearable circadian sensor device may be "installed", that is, configured for and worn by a person. The wearable sensor can include the same components as the wall sensors, but also may have more or fewer features. A basic sensor can include a spectral sensor, a battery, and a communications interface. An image sensor and the signature and hi-rez spectral data can be included in some embodiments of the worn sensor, but can be omitted in others.

At 302, setup, which can include calibration, is performed. Circadian sensor devices can be setup to communicate with the cloud and with the circadian lighting. Alternatively, the CSDs can be setup to communicate directly with a lighting controller which controls the circadian lighting. A calibration run, e.g., using image sensors, can characterize the room, including identification of window locations, etc. Calibration with a high-resolution spectral device can be used to determine a high-resolution output spectrum for the circadian lighting; calibration using the installed CSDs can be used to determine a low-resolution spectral signature for the circadian lighting.

At 303, the circadian sensor system is operated to track spectral and image data to determine the person's position, gaze direction, and seen (low resolution) circadian spectrum. At 304, the circadian lighting signature is used to determine the contribution of the circadian lighting to the seen spectrum. The high-resolution spectrum information then allows determination of a high-resolution spectral contribution of the circadian lighting to the overall seen spectrum.

At 305, the circadian lighting is set or adjusted as appropriate for meeting a circadian goal for the day for the person. The sequence from 303-305 can be repeated at least until the circadian-stimulus goal is met. A circadian health algorithm is applied to current patient health data and accumulated circadian stimulus, and a circadian dosage schedule is set or adjusted.

In the meantime, at 306, the effectiveness of the determined dosage schedules can be evaluated, e.g., based on comparisons of before and after patient health data. At 307, machine learning is used to optimize the circadian health algorithm for the patient based using effectiveness as the figure of merit.

Daytime light exposure can consolidate and increase nighttime sleep efficiency, while increasing daytime wakefulness and reducing evening agitation. The sleep/wake pattern is directly driven by the timing signals generated by the suprachiasmatic nuclei (SCN), which is known to be compromised by aging and AD. Circadian rhythm amplitude may be reduced after the age of 50. Some of the neural processes involved in entrainment may be dysfunctional or less effective as people age. Disturbances in circadian rhythms leading to poor sleep in older adults can be the result of dysfunctional circadian pathways or a pathway that cannot process light information with as much fidelity.

Older adults not only have reduced optical transmission at short wavelengths, which is maximally effective for the circadian system, they also lead a more sedentary indoor lifestyle, with less access to bright light during the day. In fact, middle-aged adults receive approximately 58 minutes of bright light per day while older adults in assisted living facilities receive bright light for only 35 minutes per day. Finally, changes in the amplitude and timing of melatonin and core body temperature rhythms may occur in older adults. Lower amplitude of melatonin rhythms may be associated with reduced sleep efficiency and deterioration of internal circadian rhythms, such as hormone production, alertness, and performance.

To maintain synchronization in the face of these physiological changes, the circadian health system provides for increasing the strength of the light stimulus. In addition, the circadian health system provides for an intervention that is maximally effective for entraining the circadian systems of those with Alzheimer's Disease and Alzheimer's Disease Related Dementias (AD/ADRD). A 24-hour light-dark pattern incident on the retina is the most efficacious stimulus for entraining the circadian system in humans. In fact, a carefully orchestrated light-dark pattern has been shown in several controlled studies of older populations, with and without ADRD, to be a powerful nonpharmacological tool to improve sleep efficiency and consolidation. While the focus herein is on AD/ADRD patients, the benefits of the invention also apply to others, e.g., including coal miners and shift workers.

Light is formally defined as optical radiation reaching the human retina that provides visual sensation. All current light sources and light meters are calibrated based on the characteristics of the light affecting our visual systems. The ideal characteristics for vision are, however, quite different from those that are most effective for stimulating the circadian system. In brief, the quantity of polychromatic white light necessary to activate the circadian system is significantly greater than the amount that activates the visual system (measured through melatonin suppression or phase shift). The spectral sensitivity of the circadian system peaks at short wavelengths, while the visual system is most sensitive to the middle wavelength portion of the visible spectrum.

Operation of the visual system does not depend significantly on the timing of light exposure; it responds well to a light stimulus at any time of the day or night. However, depending on the timing of light exposure, light can phase advance or phase delay the biological clock. In addition, while the visual system responds to a light stimulus very quickly (less than one second), the duration of light exposure needed to affect the circadian system can take much longer. For example, to achieve measurable melatonin suppression from exposure to a moderate amount of light in young adults, the required duration of light exposure is at least 5 to 10 minutes.

For the visual system, spatial light distribution is critical (e.g., when reading black text on white paper), while the circadian system does not respond to spatial patterns. The short-term history of light exposure affects the circadian system's sensitivity to light. For example, the higher the exposure to light during the day (e.g., 4 hours per day for one week to outdoor light), the lower the sensitivity of the circadian system to light at night, as measured by nocturnal melatonin suppression.

The spectral irradiance at the cornea can be converted into circadian light (CL), which is comparable to photopic illuminance but weighted by the spectral sensitivity of the human circadian system as measured by acute melatonin suppression after a 1-hour exposure. The circadian stimulus (CS) can then be determined; CS reflects the effectiveness of the spectrally weighted irradiance at the cornea from threshold (CS=0.1) to saturation (CS=0.7). While CS can be based on measurements of acute melatonin suppression, acute melatonin suppression and phase shifting of melatonin rhythms follows similar threshold and saturation response characteristics. Accordingly, the effectiveness of various light sources for activating the circadian system can be predicted.

Exposure to a CS≥0.3 at the eye, for at least 1 hour in the morning, improves sleep, mood, and behavior in AD/ADRD patients, submariners, teenagers, and healthy older adults. However, compliance can be an issue, especially with populations like AD/ADRD patients. Given that many AD/ADRD patients stay in the same place for most of the day, the ability of the circadian health system to continuously monitor a living space can reduce the burden on patients and provide useful information to caregivers.

Light intensity and spectrum are measured by the CSD. Depending on the embodiment, patient health data can be entered either at a CSD's touch screen using an app to communicate directly or via the cloud to a CSD or the controller. These data are inputs for the algorithm that calculates new target CS dosages for patients. Wireless control signals are then sent to connected lighting to initiate a closed-loop control process that adjusts lighting level and spectrum to match target CS dosages. Updated control signals are sent to connected lighting as sensor and patient health data are updated.

Circadian health system 100 provides direct health benefits to patients by automatically controlling lighting conditions to optimize CS levels. Circadian health system 100 provides active closed-loop lighting control systems that improve patient health outcomes based on established correlations between CS dosages and human health parameters. Based on inputs, (that might include time-of-day, occupants' current daily lighting exposure, caregiver inputs on patient health and historical lighting conditions in the space) an algorithm in the CSD can adjust the level and/or spectrum of color-tunable lights within the space to achieve a desired CS exposure. As more data between CS and health outcomes is gathered, these CS targets can be updated. CHS 100 uses are proposing to utilize machine learning algorithms to assist in establishing CS targets that optimize patient health outcomes.

CHS 100 can help researchers collect a much larger and more accurate dataset on the CS of AD/ADRD patients. The CSDs can be used to collect data in real-time through a secure cloud-connected network. This allows researchers to analyze data during testing, minimize interactions with and disruption to test subjects, and facilitate data collection at scale as the device is commercialized.

Caregivers can directly record patient health parameters with the CSD. For example, caregivers can be prompted to answer several basic questions about the patients' sleep, mood, and cognition using the touch screen display of a CSD or an app. These results would be automatically added to the CHS cloud-connected database as associated with the appropriate CS-related environmental data for the space. The data collected at the CHS is anticipated to augment rather than replace the more detailed and rigorous patient health data provided by health assessments collected by caregivers or researchers. The CHS-collected data is envisioned to provide real-time, quantitative data that can be associated with and compared to CS environmental data to adjust patient lighting conditions.

Caregivers can input quantitative data directly into the CSD touchscreen or app on key patient health parameters (e.g., sleep quality, cognitive function). With these inputs, detailed measurements on patient environmental conditions (as measured by CSDs) can be associated with basic details on patient health (as provided by caregivers) in a unified database.

CSDs can push data, e.g., periodically, to the controller or to the cloud via the gateway. CSD data can also be accessed remotely by accessing and downloading internal log files from individual RADS. In addition, a CHS app can be used to automatically and securely collect data from all networked CSDs. Versions of the app run on web browsers and phone operating systems. This app includes functionality for multiple administrative users (e.g., full view of all data for development teams; company-specific dashboards for specific clients; site-specific dashboards for caregivers). The app allows for remote control of connected devices (e.g., allows caregivers to adjust CS targets to specific patients individually and remotely) as well as provide a suite of real-time data analytics graphs comparing CS dosage to health outcomes).

Algorithms that will be capable of making adjustments to the intensity and spectrum of the connected lighting systems are based on inputs that include environmental conditions collected by the CSDs and patient health data, as collected by the CHS patient health status input system. These algorithms fine-tune CS dosage to optimize patient health outcomes.

Some of the calibration data collected is inherent to the lamps/luminaires used (e.g., correlations between the command signals sent to the lamp and the absolute flux it produces) while other data can be dependent on the installation application (e.g., the impact of flux changes by each lamp at the CSDs).

The CHS system actively controls the tailored light intervention (TLI) to provide the ideal dosage of CS and to automatically turn on specific lights at participants' wakeup times (but no later than 09:00 am). Herein, "tailored light intervention" means designing a lighting system and control settings that provide light therapy. For example, TLI can remain on during the day, e.g., providing 6500-9000 Kelvin (K) bluish white light; the TLI switches off automatically at 06:00 pm; then, the yellowish (warm) white lights will come on. A manual override switch can be provided for emergencies and unanticipated contingencies. See Table 1 below.

TABLE 1

TLI and comparison lighting characteristics

| Intervention | Time of Day | Spectrum | Light Level at Eye | Timing/ Duration |
| --- | --- | --- | --- | --- |
| TLI (active) | Day | 6500-9000K (bluish white) | 300-400 lux | Waking to 18:00 |
| | Evening | <2700K (warm white) | <50 lux | 18:00 to bedtime |
| Comparison | Day | <2700K (warm white) | <50 lux | Waking to 18:00 |
| | Evening | <2700K (warm white) | <50 lux | 18:00 to bedtime |

The present invention provides for several variations of CSDs. A basic CSD embodiment provides a scientific or medical device designed specifically for researchers, medical providers, architects, building managers and related practitioners to measure the circadian stimulus (CS) associated with specific locations in buildings. This CSD is particularly applicable to nursing home facility administrators, medical researchers, caregivers, and healthcare professionals with a device designed specifically for nursing home applications for Alzheimer's patients.

An HVAC-connected CSD embodiment includes HVAC (heating, ventilation, and air conditioning) control and smart grid connectivity. This provides hyper-local sensors to HVAC system controls. Smart grid connectivity allows the grid to see connected loads as controllable assets that could be used to increase grid flexibility and promote power sector decarbonization.

Another CSD combines CS measurement with closed-loop control of circadian lighting. This CSD automatically adjusts circadian lighting systems to optimize the CS of nearby users. A more advanced version provides photopic and circadian lighting control with Smart Grid Connectivity. This CSD provides a platform for users to automatically adjust their electric lighting to customize/optimize both their photopic and circadian lighting characteristics.

The CHS application supports various CSD and CHS products. There is both a feature-limited free version of this service as well as a full-featured subscription version. Customers interested in a deeper dive into CS analytics, related health outcomes, usage patterns, system efficiencies, grid optimization, or other specialty areas pay monthly fees to access these results based on the number of devices under control.

Circadian is one type of biological system that is impacted by light but not the only one and the impacts of light and spectrum can be different from the different human, animal and plant biological systems. Aspects of the invention apply to these other light-impacted biological systems as well as to circadian systems.

UL (formerly, Underwriters Laboratories) issued a standard that encourages the use of modeling to estimate CS in designing spaces as well as mechanisms to verity that CS targets are achieved after lighting systems are installed. The present invention provides for such modeling.

Herein, "A is based on B" means that A is partially or totally based on B, and does not preclude that A may be based on factors other than. B as well. Herein, all art labeled "prior art", if any, is admitted prior art; all art not labeled "prior art", if any, is not admitted prior art. The illustrated embodiments, variations thereupon, and modifications thereto are provided for by the present invention, the scope of which is defined by the following claims.

What is claimed is:

1. A circadian sensor system comprising:
    a low-resolution incident-light spectral sensor that provides low-resolution incident-light spectra, the low-resolution incident-light spectra having a low incident-light spectral resolution;
    a data analyzer for converting the low-resolution incident-light spectra to high-resolution source circadian spectra of a circadian light source, the high-resolution source circadian spectra having a high source circadian spectral resolution, the high source circadian spectral resolution being higher than the low incident-light spectral resolution, the converting being based on:
        a circadian low-resolution source signature of the circadian light source for determining low-resolution source spectra of the circadian light source based on the low-resolution incident-light spectra, the low-resolution source signature having a low source signature spectral resolution that is lower than the high source circadian spectral resolution, and
        a high-resolution source circadian profile for determining the high-resolution source circadian spectra based on the low-resolution source spectra, the high-resolution source circadian profile having a high source profile spectral resolution that is higher than the low source signature spectral resolution and higher than the low incident-light spectral resolution; and
    a wireless communications interface for wirelessly transmitting spectral data representing or based on the high-resolution source circadian spectra.

2. The circadian sensor system of claim 1 wherein the wireless communications interface is configured to communicate with the circadian light source.

3. The circadian sensor system of claim 2 wherein the wireless communications interface communicates commands for controlling the circadian light source.

4. The circadian sensor system of claim 1 further comprising storage that stores circadian goal data representing or serving as a basis for calculating a remaining amount of exposure to circadian light required by a respective person.

5. The circadian sensor system of claim 1 further comprising a battery for powering the low-resolution incident-light spectral sensor and the wireless communications interface.

6. The circadian sensor system of claim 1 wherein the wireless communications interface is configured to wirelessly communicate via a gateway.

7. The circadian sensor system of claim 6 wherein the wireless communications interface is configured to transmit the spectral data including the high-resolution source circadian spectra to a cloud via the gateway.

8. The circadian sensor system of claim 7 wherein the wireless communications interface is configured to transmit the spectral data via the gateway to a controller for the circadian light source.

9. The circadian sensor system of claim 6 further comprising plural circadian sensor devices (CSDs), the plural CSDs including respective incident-light spectral sensors and respective wireless communications interfaces, the plural CSDs including a first CSD including the low-resolution incident-light spectral sensor and the wireless communications interface, each of the wireless communications interfaces communicating via the gateway.

10. The circadian sensor system of claim 9 further comprising a circadian lighting controller for controlling the circadian light source, the plural CSDs communicating the spectral data to the circadian lighting controller via the gateway, the circadian lighting controller controlling the circadian light source based on the spectral data received from the plural CSDs.

11. The circadian sensor system of claim 1 comprising plural circadian sensor devices (CSDs) and a circadian lighting controller for controlling the circadian light source, the plural CSDs including respective incident-light spectral sensors and respective wireless communications interfaces, the plural CSDs including a first CSD including the low-resolution incident-fight spectral sensor and the wireless communications interface, each of the wireless communications interfaces transmitting the spectral data to the circadian lighting controller, the circadian lighting controller controlling the circadian light source based on the spectral data received from the plural CSDs.

12. The circadian sensor system of claim 11 wherein the plural CSDs include at least one CSD attached to a wall and at least one wearable CSD to be worn by a person, the circadian lighting controller controlling the circadian light source based on the spectral data including data received from the CSD attached to the wall and from the wearable CSD.

13. A circadian light control process comprising:
tracking, using a low-resolution incident-light spectral sensor having a low sensor spectral resolution, incident light at a location of a person to yield low-resolution incident-light spectra having a low incident-light spectral resolution;
determining, based on the low-resolution incident-light spectra and using a low-resolution source signature of a circadian light source, low-resolution source spectra, the low-resolution source signature having a low source-signature spectral resolution, the low-resolution source spectra having a low source spectra resolution;
determining, based on the low-resolution source spectra and using a high-resolution source circadian profile, high-resolution source circadian spectra, the high-resolution source circadian spectra having a high source circadian resolution, the high source circadian resolution-being higher than the low source spectral resolution and higher than the low source signature spectral resolution; and
adjusting circadian lighting at the location of the person based on the high-resolution source circadian spectra.

14. The circadian light control process of claim 13 wherein the tracking is performed using a circadian sensor device (CSD) worn by the person, the CSD including the low-resolution incident-light spectral sensor.

15. The circadian light control process of claim 14 wherein the circadian lighting is controlled based on location data provided by the CSD.

16. The circadian light control process of claim 13 wherein the tracking is performed by plural circadian sensor devices (CSDs) located at respective positions in a room, the CSDs including respective incident-light spectral sensors, one of the plural circadian sensor devices including the low-resolution incident-light spectral sensor.

17. The circadian light control process of claim 16 wherein the CSDs are mounted on respective different walls of the room.

18. The circadian light control process of claim 16 further comprising using image sensors to determine the location of the person in the room.

19. The circadian light control process of claim 18 wherein the image sensors are included in respective ones of the CSDs.

20. The circadian light control process of claim 19 further comprising using the image sensors to determine a gaze direction of the person.

21. The circadian light control process of claim 20 further comprising using the CSDs to determine a circadian stimulus (CS) of the person.

22. The circadian light control process of claim 13 further comprising evaluating an effectiveness of an adjustment to the circadian lightning.

23. The circadian light control process of claim 22 further comprising using machine learning to optimize an algorithm for adjusting the circadian lighting based on the evaluated effectiveness of the adjustments to the circadian lighting.

24. The circadian light control process of claim 13 wherein the tracking is performed by plural circadian sensor devices (CSDs) including at least one CSD attached to a wall and at least one wearable CSD to be worn by the person, a circadian lighting controller controlling the circadian light source based on sensor data including data received from the CSD attached to the wall and from the wearable CSD.

25. The circadian light control process of claim 13 further comprising determining at least one of the low-resolution source signature and the high-resolution source circadian profile during a calibration procedure.

26. The circadian sensor system of claim 1 wherein at least one of the low-resolution source signature and the high-resolution source circadian profile was determined during a calibration procedure.

* * * * *